(12) United States Patent
Umekawa et al.

(10) Patent No.: US 10,376,223 B2
(45) Date of Patent: Aug. 13, 2019

(54) LIVING-BODY INFORMATION MEASUREMENT DEVICE AND NON-TRANSITORY COMPUTER READABLE MEDIUM

(71) Applicant: FUJI XEROX CO., LTD., Tokyo (JP)

(72) Inventors: Hideyuki Umekawa, Kanagawa (JP); Kazuhiro Sakai, Kanagawa (JP); Manabu Akamatsu, Kanagawa (JP); Tomoaki Kojima, Kanagawa (JP)

(73) Assignee: FUJI XEROX CO., LTD., Minato-ku, Tokyo (JP)

( * ) Notice: Subject to any disclaimer, the term of this patent is extended or adjusted under 35 U.S.C. 154(b) by 368 days.

(21) Appl. No.: 15/226,371

(22) Filed: Aug. 2, 2016

(65) Prior Publication Data
US 2017/0273575 A1   Sep. 28, 2017

(30) Foreign Application Priority Data

Mar. 28, 2016  (JP) .................................. 2016-064454
Mar. 28, 2016  (JP) .................................. 2016-064455
Mar. 28, 2016  (JP) .................................. 2016-064456

(51) Int. Cl.
*A61B 5/00*  (2006.01)
*A61B 5/026*  (2006.01)
(Continued)

(52) U.S. Cl.
CPC .......... *A61B 5/7278* (2013.01); *A61B 5/0261* (2013.01); *A61B 5/14551* (2013.01);
(Continued)

(58) Field of Classification Search
CPC ... A61B 5/7278; A61B 5/725; A61B 5/14551; A61B 5/0261; A61B 5/7275;
(Continued)

(56) References Cited

U.S. PATENT DOCUMENTS 5,497,769 A * 3/1996 Gratton ................ A61B 5/0059
356/41
5,598,841 A * 2/1997 Taniji ................... A61B 5/0261
600/342
(Continued)

FOREIGN PATENT DOCUMENTS

JP         07-265284 A    10/1995
JP          4475601 B2     6/2010

*Primary Examiner* — Eric F Winakur
*Assistant Examiner* — Abid A Mustansir
(74) *Attorney, Agent, or Firm* — Sughrue Mion, PLLC

(57) ABSTRACT

Provided is a living-body information measurement device including a first light emitting element and a second light emitting element each that emits different light in wavelength, a light receiving element that receives the light emitted from the first light emitting element and the second light emitting element, a control unit that controls an emission period of each of the first light emitting element and the second light emitting element so that the number of times of emission of the second light emitting element per unit time is less than the number of times of emission of the first light emitting element per unit time, and a measuring unit that measures plural living-body information based on the light received in the light receiving element.

16 Claims, 8 Drawing Sheets

(51) Int. Cl.
*A61B 5/0295* (2006.01)
*A61B 5/1455* (2006.01)

(52) U.S. Cl.
CPC ............ *A61B 5/725* (2013.01); *A61B 5/0295* (2013.01); *A61B 5/14552* (2013.01); *A61B 5/7203* (2013.01); *A61B 5/7225* (2013.01); *A61B 5/7257* (2013.01); *A61B 5/7275* (2013.01); *A61B 2562/0238* (2013.01)

(58) Field of Classification Search
CPC .............. A61B 5/14552; A61B 5/7203; A61B 2562/0238; A61B 5/0295; A61B 5/7225; A61B 5/7257
See application file for complete search history.

(56) References Cited

U.S. PATENT DOCUMENTS

2009/0005662 A1* 1/2009 Petersen ............ A61B 5/14551
600/323
2010/0056887 A1 3/2010 Kimura et al.

\* cited by examiner

LIVING-BODY INFORMATION MEASUREMENT DEVICE AND NON-TRANSITORY COMPUTER READABLE MEDIUM

CROSS-REFERENCE TO RELATED APPLICATIONS

This application is based on and claims priority under 35 USC 119 from Japanese Patent Application Nos. 2016-064454 filed Mar. 28, 2016, 2016-064455 filed Mar. 28, 2016, and 2016-064456 filed Mar. 28, 2016.

BACKGROUND

Technical Field

The present disclosure relates to a living-body information measurement device and a non-transitory computer readable medium.

SUMMARY

According to an aspect of the invention, there is provided a living-body information measurement device including:

a first light emitting element and a second light emitting element each that emits different light in wavelength;

a light receiving element that receives the light emitted from the first light emitting element and the second light emitting element;

a control unit that controls an emission period of each. of the first light emitting element and the second light emitting element so that the number of times of emission of the second light emitting element per unit time is less than the number of times of emission of the first light emitting element per unit time; and a measuring unit that measures plural living-body information based on the light received in the light receiving element.

BRIEF DESCRIPTION OF THE DRAWINGS

Exemplary embodiments of the present invention will be described in detail based on the following figures, wherein.

DETAILED DESCRIPTION

Figure 1:
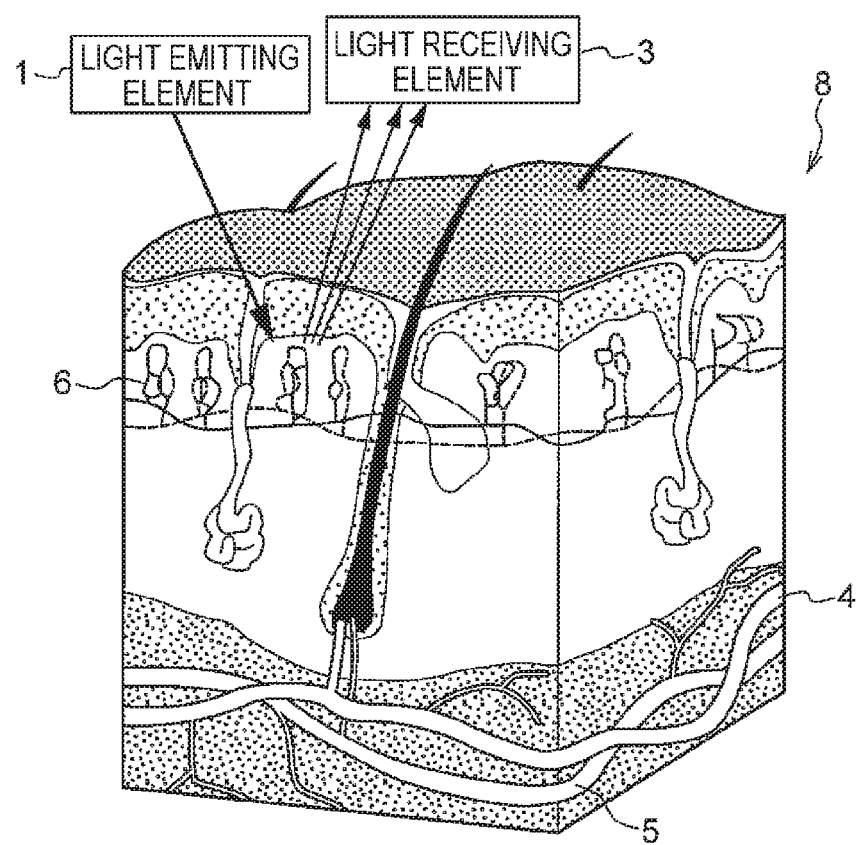
FIG. 1 is a schematic diagram illustrating a measurement example of blood flow information and an oxygen saturation in the blood.

Hereinafter, exemplary embodiments of the present disclosure will be described in detail with reference to the accompanying drawings. Throughout the drawings, the same elements, operations or functions are denoted by the same reference numerals or symbols and explanation thereof will not be repeated for the purpose of brevity.

First, referring to FIG. 1, a method of measuring a blood flow information and an oxygen saturation in the blood, as one example of living-body information on the blood among living-body information, will be described with reference to FIG. 1.

As illustrated in FIG. 1, when light is emitted from a light emitting element 1 to penetrate through the body of a patient (a living body 8) and is received in a light receiving element 3, blood flow information and an oxygen saturation in the blood are measured by using the intensity of light reflected by or transmitted through arteries 4, veins 5 and capillaries 6 spread throughout the living body 8, i.e., measured using the amount of reflected or transmitted light received in the light receiving element 3.

(Measurement of Blood Flow Information)

Figure 2:
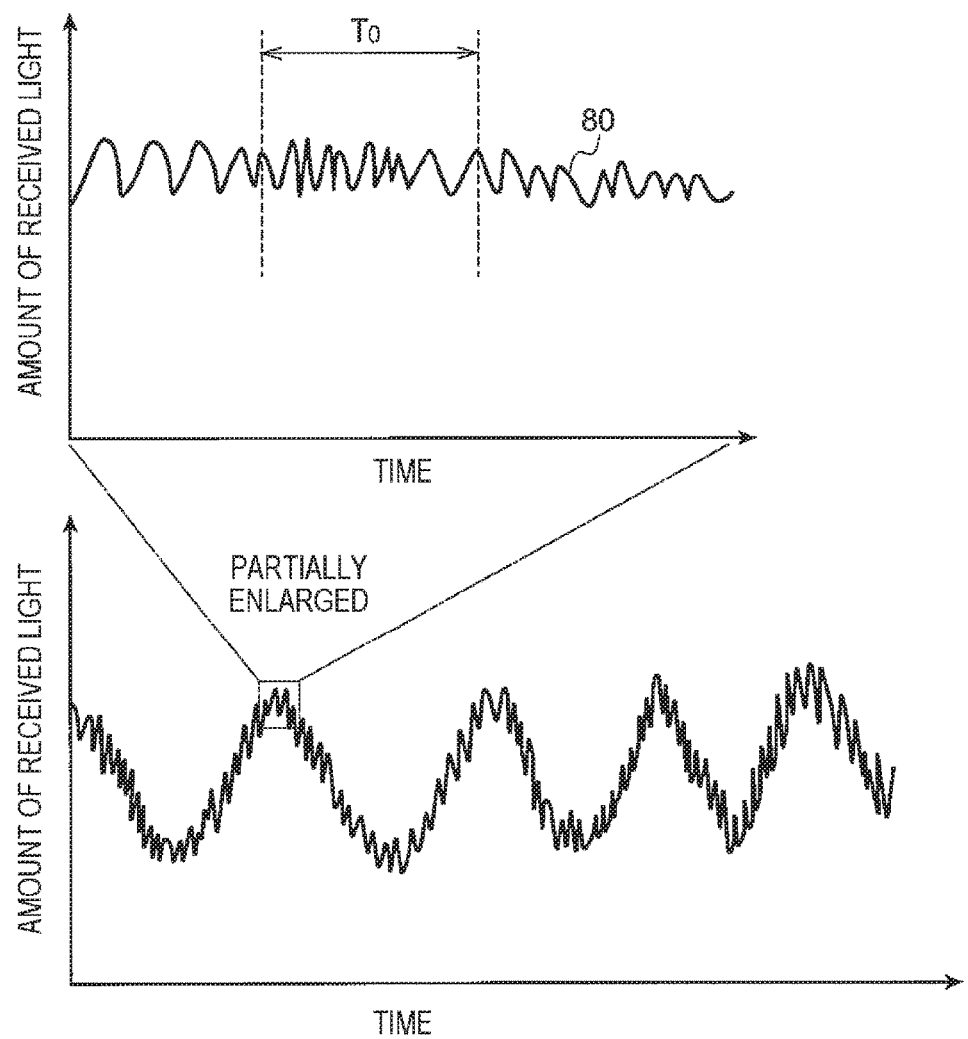
FIG. 2 is a graph illustrating one example of a change in an amount of received light due to reflected light from a living body.

FIG. 2 is one example of a curve 80 that represents the amount of reflected light received by the light receiving element 3. In the graph of FIG. 2, the horizontal axis represents time and the vertical axis represents an output of the light receiving element 3, i.e., the amount of light received by the light receiving element 3.

As illustrated in FIG. 2, the amount of light received in the light receiving element 3 is changed with time. This phenomenon maybe attributed to three optical phenomenons appearing when the living body 8 including the blood vessels is irradiated with light.

The first optical phenomenon is a change in absorption of light due to a change in volume of blood existing in a blood vessel under measurement by pulsation. The blood contains blood cells such as red blood cells and moves through the blood vessels such as capillaries 6. Therefore, the number of blood cells moving through the blood vessels may be changed with the change in the volume of the blood, which may have an influence on the amount of light received in the light receiving element 3.

As the second optical phenomenon, an influence by a Doppler shift may be considered.

Figure 3:
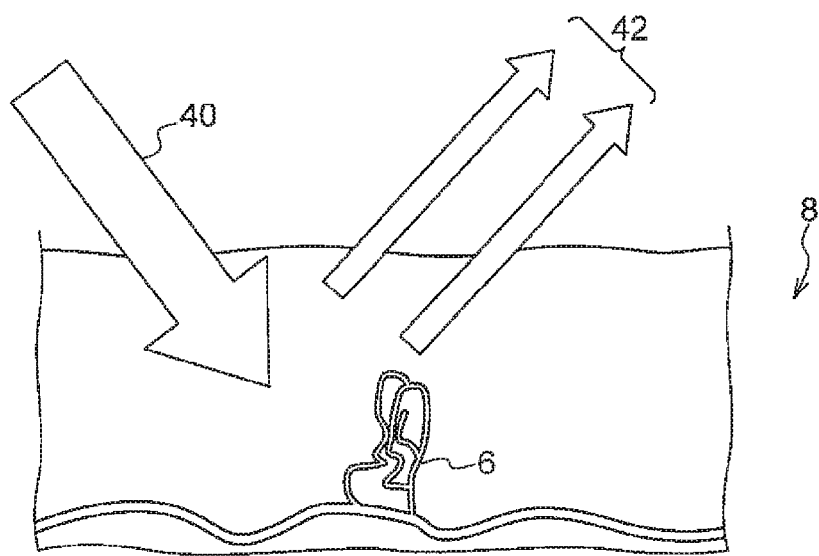
FIG. 3 is a schematic diagram used to explain a Doppler shift which occurs when a blood vessel is irradiated with a laser beam.

As illustrated in FIG. 3, for example, when a region including the capillaries 6 as one example of the blood vessels is irradiated with a coherent light 40 of a frequency $\omega_0$ such as a laser beam from the light emitting element 1, a scattered light 42 scattered by the blood cells moving through the capillaries 6 causes a Doppler shift having a frequency difference $\Delta\omega_0$ determined by a moving speed of the blood cells. In the meantime, the scattered light 42 scattered by the tissues (stationary tissues) such as the shins which do not contain moving bodies such as blood cells maintains the same frequency $\omega_0$ as the irradiated laser beam. Therefore, the frequency $\omega_0+\Delta\omega_0$ of the laser beam scattered by the blood vessels such as the capillaries 6 interferes with the frequency $\omega_0$ of the laser beam scattered by the stationary tissues. Due to such interference, a beat signal having the frequency difference $\Delta\omega_0$ is generated and observed in the light receiving element 3, and as a result, the amount of light received in the light receiving element 3 is changed with time. The frequency difference $\Delta\omega_0$ of the beat signal observed in the light receiving element 3 falls within a frequency range having the upper limit of about several tens kHz, although the frequency difference $\Delta\omega_0$ depends on the moving speed of the blood cells.

The third optical phenomenon may be an influence by speckles.

Figure 4:
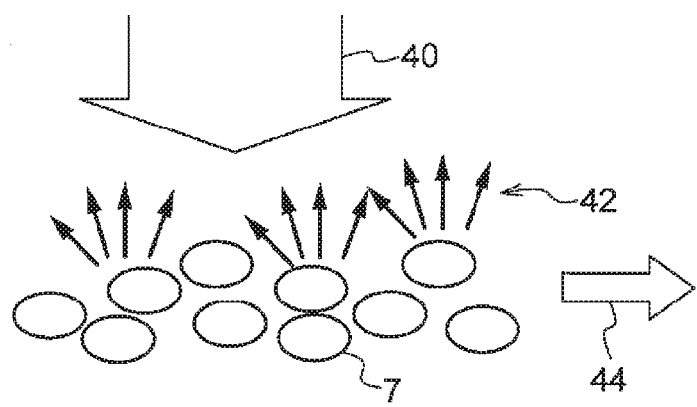
FIG. 4 is a schematic diagram used to explain speckles which occur when a blood vessel is irradiated with a laser beam.

As illustrated in FIG. 4, when the blood cells 7 such as the red blood cells moving through a blood vessel in a direction indicated by an arrow 44 are irradiated with coherent light 40 such as a laser beam from the light emitting element 1, the laser beam striking on the blood cells 7 is scattered in different directions. The scattered beams have different phases and accordingly interfere with one another in a random manner. This results in a light intensity distribution having a random spotted patterns. The light intensity distribution pattern formed in this way is called a "speckle pattern."

As described above, since the blood cells 7 move through the blood vessel, a state of light scattering in the blood cells 7 is changed and accordingly the speckle pattern is changed with time. As a result, the amount of light received in the light receiving element 3 is changed with time.

Figure 5:
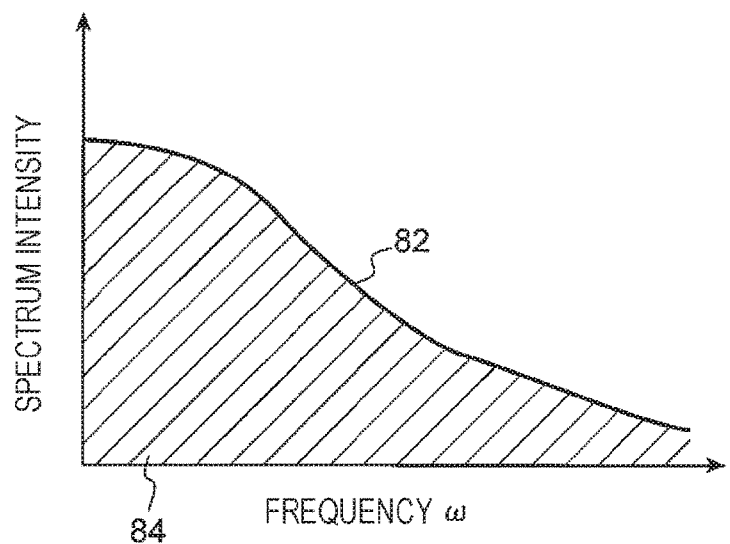
FIG. 5 is a graph illustrating one example of a spectrum distribution with respect to a change in an amount of received light.

Next, one example of a method of obtaining information on a blood flow will be described. When the amount of received light of the light receiving element 3 changed with time is obtained as illustrated in FIG. 2, the data included in a range of a predetermined unit time $T_0$ are extracted and then subjected to, for example, the fast Fourier transform (FFT), thereby obtaining a spectrum distribution for each frequency $\omega$. FIG. 5 is a graph showing a curve 82 representing an example of the spectrum distribution for each frequency $\omega$ in the unit time $T_0$. In the graph of FIG. 5, the horizontal axis represents a frequency $\omega$ and the vertical axis represents a spectrum intensity.

Here, the blood volume is proportional to a value obtained by normalizing the area of power spectrum, which is indicated by a hatched region 84 surrounded by the horizontal axis and the vertical axis of the curve 82, with the total light amount. In addition, since a blood velocity is proportional to a frequency mean value of the power spectrum represented by the curve 82, the blood velocity is proportional to a value obtained by dividing a value, which is obtained by integrating a product of the frequency $\omega$ and the power spectrum at the frequency $\omega$ with respect to the frequency $\omega$, by the area of the hatched region 84.

In addition, since the blood flow is represented by a product of blood volume and blood velocity the blood flow may be obtained from a calculation formula of the blood volume and blood velocity. The blood flow, the blood velocity and the blood volume are one example of the blood flow information without being limited thereto.

Figure 6:
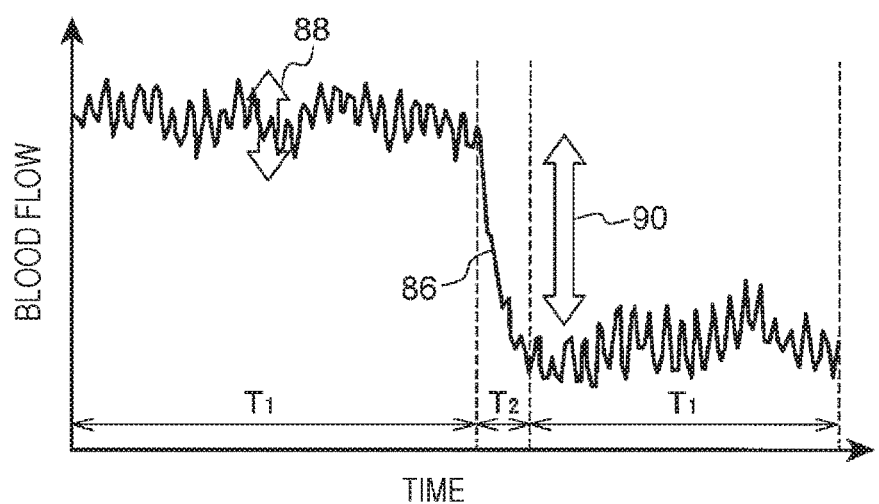
FIG. 6 is a graph illustrating one example of a change in blood flow.

FIG. 6 is a graph showing a curve 86 representing an example of the calculated change in the blood flow per unit time $T_0$. In the graph of FIG. 6, the horizontal axis represents time and the vertical axis represents a blood flow.

As illustrated in FIG. 6, while the blood flow varies with time, the trend of variation may be classified into two types. For example, in FIG. 6, a variation range 90 of blood flow in an interval $T_2$ as larger than a variation range 88 of blood flow in an interval $T_1$. This may be because the change of flood flow in the interval $T_1$ is mainly due to the motion of a pulse, whereas the change of the flood flow in the interval $T_2$ is due to, for example, the congestion or the like.

(Measurement of Oxygen Saturation)

Next, measurement of an oxygen saturation in the blood will be described. The oxygen saturation in the blood is an indicator that indicates a degree of hemoglobin bonded to oxygen in blood. As the oxygen saturation is reduced in the blood, a symptom such as anemia or the like is apt to occur.

Figure 7:
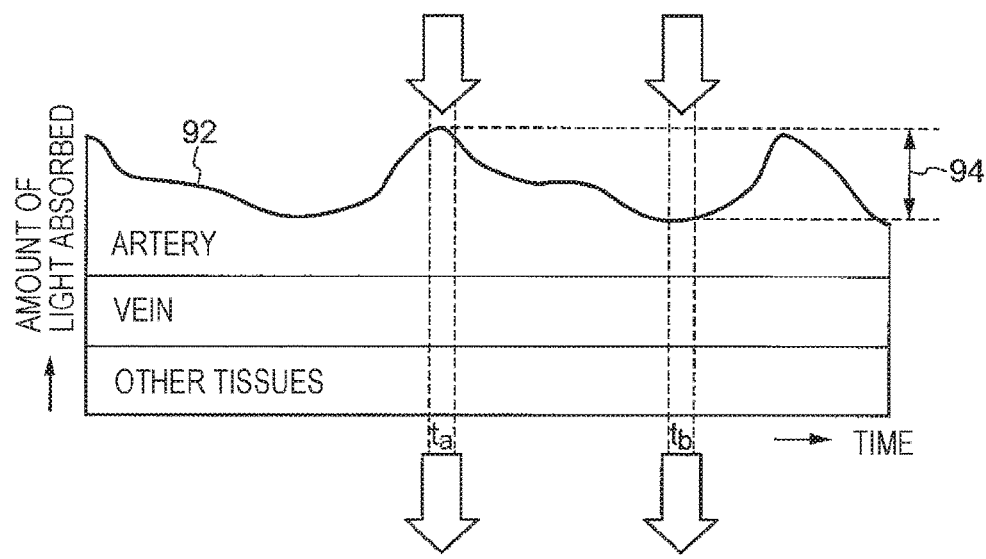
FIG. 7 is a graph illustrating one example of a change in absorbance of light absorbed in a living body.

FIG. 7 is a conceptual graph illustrating the change in absorbance of Right absorbed in, for example, the living body 8. As illustrated in FIG. 7, the amount of light absorbed in the living body 8 shows a tendency of variation with time.

In addition, referring to the contents of the variation of amount of light absorbed in the living body 8, it is known that the amount of light absorbed is mainly varied by the arteries 4 but may be negligible in other tissues including the veins 5 and the stationary tissues as compared to the arteries 4. This is because the arterial blood pumped from the heart moves through the blood vessels with a pulse wave and the arteries 4 expand/contract along the sectional direction of the arteries 4 with time, thereby causing a change in, thickness of the arteries 4. In FIG. 7, the range indicated by an arrow 94 represents a variation of amount, of light absorbed corresponding to the change in thickness of the arteries 4

In FIG. 7, assuming that the amount of received light at time $t_a$ is $I_a$ and the amount of received light at time $t_b$ is $I_b$, a variation $\Delta A$ of amount of light absorbed due to the change in thickness of the arteries 4 is expressed by the following equation (1)

$$\Delta A = \ln(I_b/I_a) \quad (1)$$

In the meantime, it is known that the hemoglobin bonded to the oxygen flowing through the arteries 4 (oxidized hemoglobin) is apt to absorb light of an infrared (IR) region having a wavelength of about 880 nm or so and the hemoglobin not bonded to the oxygen (reduced hemoglobin) is apt to absorb light of a red region having a wavelength of about 665 nm or so. Further, it is known that the oxygen saturation has a proportional relationship with a ratio of the variation $\Delta A$ of amount of light absorbed at different wavelengths.

Accordingly, in comparison with other combinations of wavelengths, by using the infrared light (IR light) and the red light, which are likely to produce a difference in amount of light absorbed between the oxidized hemoglobin and the reduced hemoglobin, to calculate a ratio of variation $\Delta A_{red}$ of amount of light absorbed when the living body 8 is irradiated with the IR light to variation $\Delta A_{IR}$ of amount of light absorbed when the living body 8 is irradiated with the red light, the oxygen saturation S is calculated according to the following equation (2). In the equation (2), k is a proportional constant.

$$S = k(\Delta A_{Red}/\Delta A_{IR}) \quad (2)$$

That is, when the oxygen saturation in the blood is calculated, plural light emitting elements 1 emitting light having different wavelengths, specifically, a light emitting element 1 emitting IR light and a light emitting element 1 emitting red light, are caused to emit light in such a manner that their emission periods do not overlap with each other, although the emission periods may partially overlap with each other. Then, the reflected light or transmitted light by each light emitting element 1 is received in the light receiving element 3 and the oxygen saturation in the blood is measured by calculating the equations (1) and (2) or known equations obtained by modifying these equations (1) and (2) from the amount of received light at respective light receiving points.

As a known equation obtained by modifying the equation (1), the variation $\Delta A$ of amount of light absorbed may be expressed as the following equation (3) by transforming the equation (1).

$$\Delta A = \ln I_b - \ln I_a \quad (3)$$

In addition, the equation (1) may be modified into the following equation (4).

$$\Delta A = \ln(I_b/I_a) = \ln(1+(I_b-I_a)/I_a) \quad (4)$$

Typically, since the relation of $\ln(I_b/I_a) \approx (I_b-I_a)/I_a$ is established from the relation of $(I_b-I_a) \ll I_a$, the equation (1) may be replaced with the following equation (5) as the variation $\Delta A$ of amount of light absorbed.

$$\Delta A \approx (I_b-I_a)/I_a \quad (5)$$

Hereinafter, when the light emitting element 1 emitting IR light and the light emitting element 1 emitting red light are required to be distinguished from each other, the light emitting element 1 emitting IR light will be referred to as a "light emitting element LD1" and the light emitting element 1 emitting red light will be referred to as a "light emitting element LD2." In addition, as one example, the light emitting element ID1 is assumed as the light emitting element 1 used for calculation of the blood flow and the light emitting elements LD1 and LD2 are assumed as light emitting elements 1 used for calculation of the oxygen saturation in the blood.

As described above, in the measurement of the blood flow, since the frequency difference $\Delta \omega_0$ of the beat signal observed in the light receiving element 3 falls within a frequency range having the upper limit of about several tens kHz, the light emitting element LD1 has to be emitting light with a frequency which is at least twice as high as the frequency difference $\Delta \omega_0$ and the reflected light by the light emitting element LD1 has to be received in the light receiving element 3.

Accordingly, considering to be combined with the measurement of the oxygen saturation in the blood, for example, after adjusting an emission frequency of the light emitting element LD2 to an emission frequency of the light emitting element LD1, a portion of the emission period of each of the light emitting element LD1 and LD2 may be overlapped with each other. However, the light emitting elements LD1 and LD2 may emit light alternately such that the emission periods of the light emitting elements LD1 and LD2 do not overlap with each other, and the amount of received light is obtained in the light receiving element 3 for every emission period of the light emitting elements LD1 and LD2 to measure the oxygen saturation in the blood.

However, when the oxygen saturation in the blood is measured, since it is known that a frequency of measurement of the amount of received light is sufficient to fall within a range of from about 30 Hz to about 1,000 Hz, the emission frequency of the light emitting element LD2 is also sufficient to fall within a range of from about. 30 Hz to about 1,000 Hz That is, it may be seen that the emission frequency of the light emitting element LD2 is set to be lower than the emission frequency of the light emitting element LD1 with no need for the light emitting element LD2 to emit light with its emission frequency adjusted to the emission frequency of the light emitting element LD1.

Hereinafter, a living-body information measurement device for measuring plural living-body information with the power less than the power consumed when the light emitting element LD1 and the light emitting element LD2 emit light in an alternating manner will be described.

Figure 8:
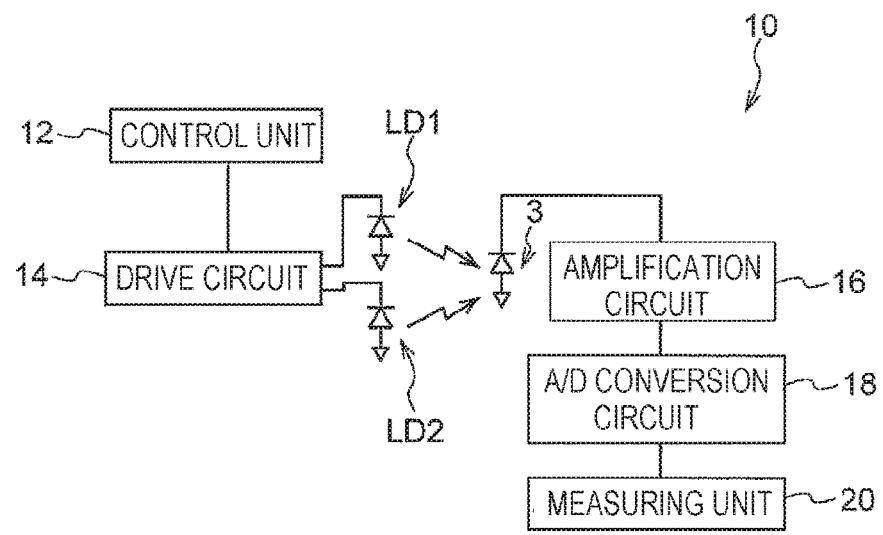
FIG. 8 is a view illustrating the configuration of a living-body information measurement device.

FIG. 8 is a view illustrating the configuration of a living-body information measurement device 10 according to an exemplary embodiment.

As illustrated in FIG. 8, the living-body information measurement device 10 includes a control unit 12, a drive circuit 14, an amplification circuit 16, an analog/digital (A/D) conversion circuit 18, a measuring unit 20, the light emitting element LD1, the light emitting element LD2, and the light receiving element 3.

The control unit 12 outputs a control signal, which controls an emission period and emission interval of each of the light emitting elements LD1 and LD2, to the drive circuit 14 including a power supply circuit for supplying drive power to the light emitting elements LD1 and LD2.

Upon receiving the control signal from the control unit 12, according to the emission period and emission interval instructed by the control signal, the drive circuit 14 supplies the drive power to the light emitting elements LD1 and LD2 so as to drive the light emitting elements LD1 and LD2.

The amplification circuit 16 amplifies a voltage corresponding to the intensity of light received in the light receiving element 3 up to a voltage level specified as an input voltage range of the A/D conversion circuit 18. In this example, the light receiving element 3 outputs a voltage corresponding to the intensity of received light. However, as another example, the light receiving element 3 may output a current corresponding to the intensity of received light In this case, the amplification circuit 16 amplifies the current output by the light receiving element 3 up to a current level specified as an input current range of the A/D conversion circuit 18.

The A/D conversion circuit 18 receives the voltage amplified by the amplification circuit 16 as an input and digitizes the amount of light received in the light receiving element 3 which is expressed as the magnitude of the voltage.

The measuring unit 20 receives the amount of received light digitized by the A/D conversion circuit 18 as an input, calculates a spectrum distribution for each frequency $\omega$ by subjecting the amount of received light emitted by the light emitting element LD1 to the FF1, and measures a blood flow by integrating the product of the frequency $\omega$ and the power spectrum at the frequency $\omega$ with respect to the frequency $\omega$.

In addition, the measuring unit 20 receives the amount of received light digitized by the A/D conversion circuit 18 as an input and manages the amount of received light emitted by the light emitting element LD1 and the light emitting element LD2 in a chronological order. Then, the measuring unit 20 measures an oxygen saturation by calculating a variation $\Delta A_{IR}$ of amount of light absorbed of the light emitting element LD1 and a variation $\Delta A_{Red}$ of amount of light absorbed of the light emitting element LD2 according to the equation (1) and calculating a ratio of amount of light absorbed variation $\Delta A_{Red}$ to amount of light absorbed variation $\Delta A_{IR}$ according to the equation (2).

Figure 9:
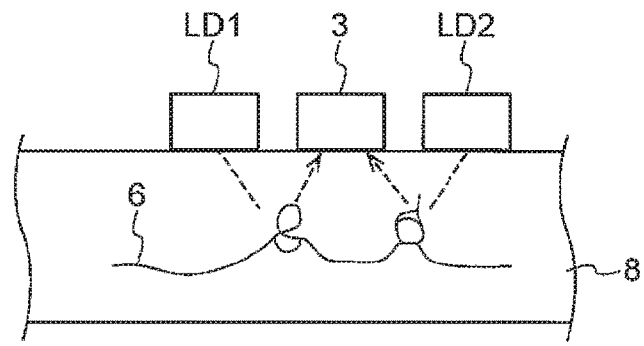
FIG. 9 is a view illustrating one example of an arrangement of a light emitting element and a light receiving element.

FIG. 9 illustrates one example of arrangement of the light emitting elements LD1 and LD2 and the light receiving element 3 in the living-body information measurement device 10. As illustrated in FIG. 9, the light emitting elements LD1 and LD2 and the light receiving element 3 are arranged side by side on the living body 8. In this example, the light receiving element 3 receives light of the light emitting elements LD1 and LD2 which is reflected at the living body 8.

Figure 10:
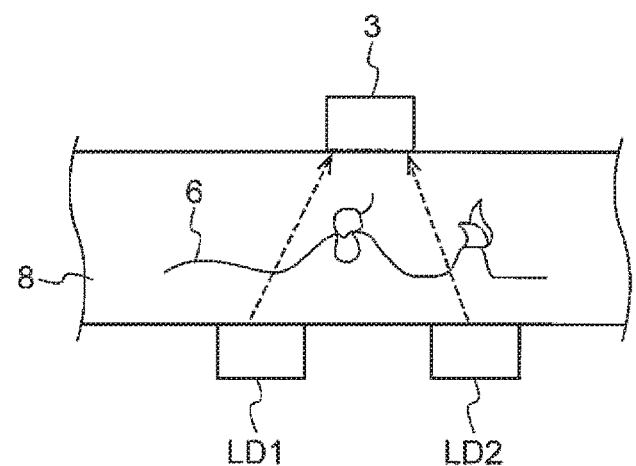
FIG. 10 is a view illustrating another example of an arrangement of a light emitting element and a light receiving element.

However, the arrangement of the light emitting elements LD1 and LD2 and the light receiving element 3 is not limited to the arrangement example of FIG. 9. For example, as illustrated in FIG. 10, the light emitting elements LD1 and LD2 may be arranged to face the light receiving element 3 with the living body 8 sandwiched therebetween. In this example, the light receiving element 3 receives light of the light emitting elements LD1 and LD2 which transmits through the living body 8.

Although in these examples the light emitting elements LD1 and LD2 are both surface-emission lasers, the light emitting elements LD1 and LD2 are not limited thereto but may be edge-emission lasers.

When a blood flow is to be measured by the measuring unit 20, since this measurement is made based on a spectrum distribution of the amount of received light according to a beat signal as described above, a laser device which may generate a beat signal more easily than different light may be preferably used for the light emitting element LD1.

However, even if the light emitted from the light emitting element LD2 is not a laser beam, since the amount of light absorbed variation $\Delta A_{Red}$ of the light emitting element LD2 may be calculated, a light emitting diode (LED) or an organic light emitting diode (OLED) may be used for the light emitting element LD2.

Next, the configuration of main parts of an electric system of the living-body information measurement device 10 according to this exemplary embodiment will be described with reference to FIG. 11.

Figure 11:
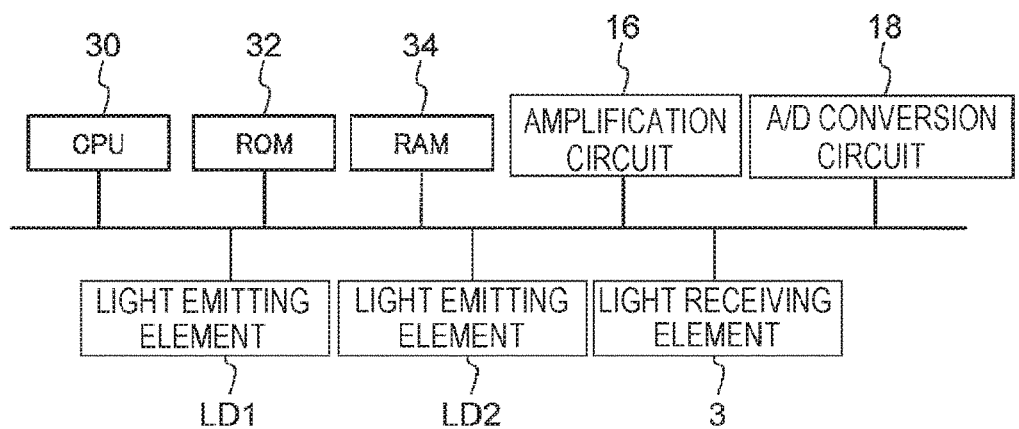
FIG. 11 is a view illustrating an exemplary configuration of main parts of an electric system of the living-body information measurement device.

As illustrated in FIG. 11, the living-body information measurement device 10 according to this exemplary embodiment includes a control unit for controlling an emission period and an emission interval of each of the light emitting element LD1 and the light emitting device LD2, and a central processing unit (CPU) 30 as one example of a measuring unit for measuring a blood flow and an oxygen saturation in the blood in the living body 8. In addition, the living-body information measurement device 10 includes a read only memory (ROM) 32 in which a variety of programs and parameters are stored, and a random access memory (RAM) 34 used as a work area or the like when the variety of programs are executed by the CPU 30.

The CPU 30, the ROM 32 and the RAM 34 are connected to one another via an internal bus 36 of the living-body information measurement device 10. In addition, the light emitting element LD1, the light emitting element LD2, the light receiving element 3, the amplification circuit 16 and the A/D conversion circuit 18 are connected to the internal bus 36.

In addition, a timer for measuring lapse time from a specified point of time is contained in the CPU 30.

Next, an operation of the living-body information measurement device 10 will be described with reference to FIG. 12.

Figure 12:
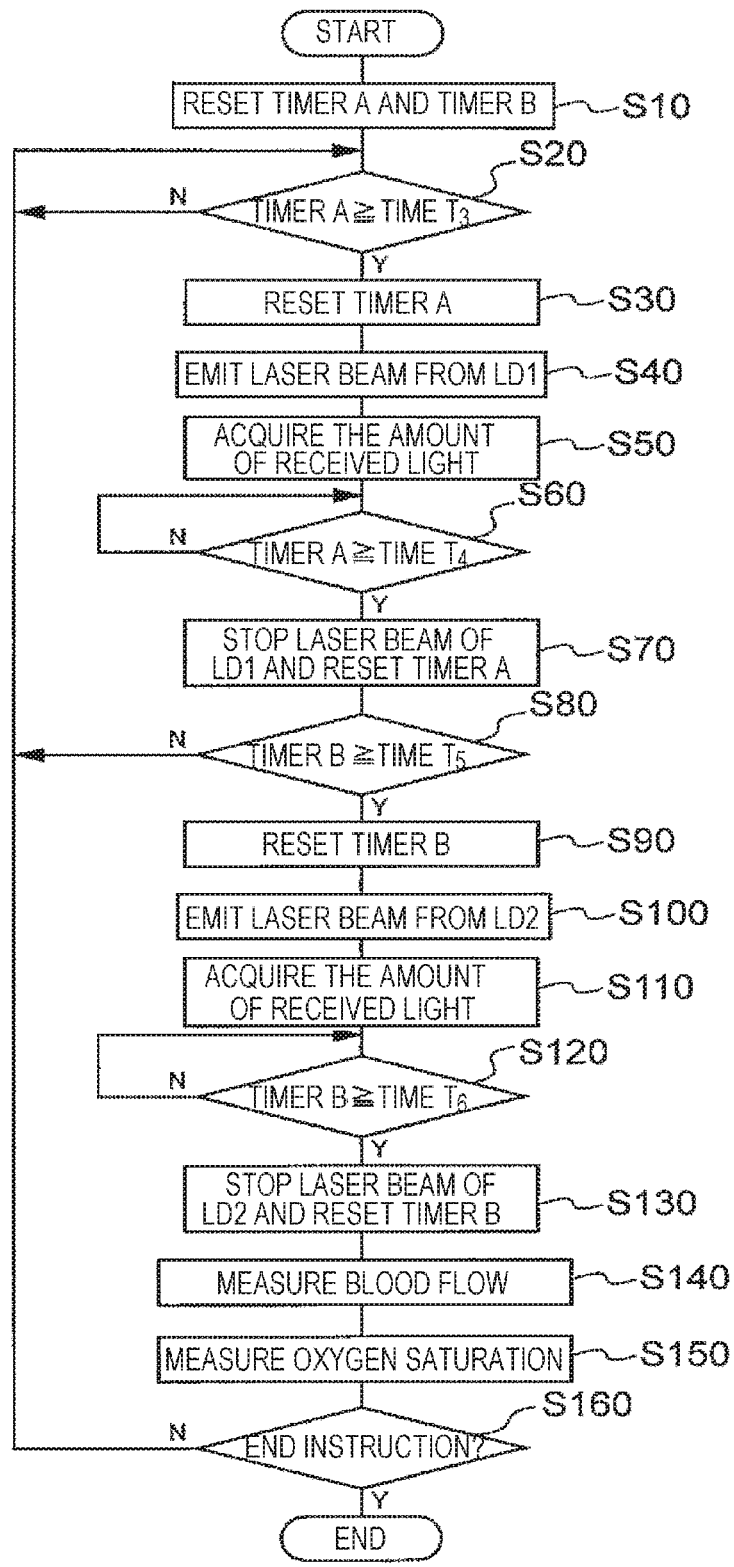
FIG. 12 is a flow chart illustrating one example of flow of living-body information measuring process.

FIG. 12 is a flow chart illustrating one example of a flow of living-body information measuring process executed by the CPU 30 when the CPU 30 receives an instruction to start measurement of living-body information. A program defining the living-body information measuring process (a living-body information measurement program) is preinstalled in, e.g., the ROM 32. In addition, it is assumed that the light emitting element LD1 and the light emitting element LD2 are both in an emission stop state where no laser beam is emitted at a point of time of start of the living-body information measurement program.

First, at Step S10, the CPU 30 resets two timers A and B contained in the CPU 30. Here, "resetting a timer" means that measurement by the timer is stopped and the timer newly starts to count the lapse time from the stop point of the timer.

At Step S20, the CPU 30 determines whether or not the timer A has elapsed time $T_3$ or more after resetting the timer A at Step S10. The time $T_3$ is a parameter stored in a preset area of the ROM 32 and determines a time interval from the emission period of the light emitting element LD1 and the next emission period thereof, i.e., an emission stop period of the light emitting element LD1.

Since the light emitting element LD1 is used for the measurement of the blood flow, the emission stop period of the light emitting element LD1 is set to a period corresponding to a frequency range with an upper limit of about several tens kHz.

When a result of the determination at Step S20 is negative, the CPU 30 repeats Step S20 and waits until the timer A has elapsed time $T_3$ or more. In the meantime, when the result of the determination at Step S20 is affirmative, the process proceeds to Step S30.

At Step S30, the CPU 30 rests the timer A.

Then, at Step S40, the CPU 30 informs the drive circuit 14 of an emission start instruction to instruct an emission start of the light emitting element LD1. Upon receiving the emission start instruction, the drive circuit 14 supplies drive power to the light emitting element LD1 and causes the light emitting element LD1 to emit a laser beam.

At Step S50, the CPU 30 acquires the amount of light, which is emitted by the light emitting element LD1 and received in the light receiving element 3 in the emission period of the light emitting element LD1, from the A/D conversion circuit 18 and stores the acquired amount of light in a preset area of the RAM 34.

At Step S60, the CPU 30 determines whether or not the timer A has expired time $T_4$ or more after resetting the timer A at Step S30. The time $T_4$ is a parameter stored in a preset area of the ROM 32 and determines a time interval until the light emitting element LD1 stops the emission after the light emitting element LD1 emits the laser beam, i.e., the emission period of the light emitting element LD1.

When a result of the determination at Step S60 is negative, the CPU 30 repeats Step S60 and waits until the timer A has elapsed time $T_4$ or more. In the meantime, when the result of the determination at Step S60 is affirmative, the process proceeds to Step S70.

At Step S70, the CPU 30 informs the drive circuit 14 of an emission stop instruction to instruct an emission stop of the light emitting element LD1. Upon receiving the emission stop instruction, the drive circuit 14 stops the supply of drive power to the light emitting element LD1 and causes the light emitting element LD1 to stop the emission of the laser beam. In addition, the CPU 30 resets the timer A.

At Step S80, the CPU 30 determines whether or not the timer B has expired time $T_5$ or more after resetting the timer B at Step S10. The time $T_5$ is a parameter stored in a preset area of the ROM 32 and determines an emission stop period of the light emitting element LD2. The time T is set to be longer than time $T_3$. Specifically, time $T_5$ may be set to meet a period corresponding to a measurement frequency of the amount of light emitted respectively from the light emitting element LD1 and the light emitting element LD2, specifically, a frequency falling within a range of from about 30 Hz to about. 1,000 Hz.

By setting time $T_5$ in this way, an emission period from the emission of the light emitting element LD2 to the next emission thereof is set to be longer than the emission period of the light emitting element LD1, as will be described later.

When a result of the determination at Step S80 is negative, the process returns to Step S20 and the CPU 30 repeats Steps S20 to S80 to cause the light emitting element LD1 to emit a laser beam over time $T_4$ every time $T_3$ during the emission stop period of the light emitting element LD2.

In the meantime, when the result of the determination at Step S80 is affirmative, the process returns to Step S90.

At the subsequent Steps S90 to S130, the same emission start operation and emission stop operation as the light emitting element LD1 illustrated in Steps S30 and S70 are performed for the light emitting element LD2.

That is, at Step S90, the CPU 30 resets the timer B.

At Step S100, the CPU 30 informs the drive circuit 14 of an emission start instruction to instruct an emission start of the light emitting element LD2. Upon receiving the emission start instruction, the drive circuit 14 supplies drive power to the light emitting element LD2 and causes the light emitting element LD2 to emit a laser beam.

At Step S110, the CPU 30 acquires the amount of light, which is emitted by the light emitting element LD2 and received in the light receiving element 3 in the emission period of the light emitting element LD2, from the A/D conversion circuit 18 and stores the acquired amount of light in a preset area of the RAM 34.

At Step S120, the CPU 30 determines whether or not the timer B has elapsed time $T_6$ or more after resetting the timer B at Step S90. The time $T_6$ is a parameter stored in a preset area of the ROM 32 and determines the emission period of the light emitting element LD2. The time $T_6$ is set to be shorter than time $T_3$ for which the length of the emission stop period of the light emitting element LD1 is set.

When a result of the determination at Step S120 is negative, the CPU 30 repeats Step S120 and waits until the timer B has expired time $T_6$ or more. In the meantime, when the result of the determination at Step S120 is affirmative, the process proceeds to Step S130.

At Step S130, the CPU 30 informs the drive circuit 14 of an emission stop instruction to instruct an emission stop of the light emitting element LD2. Upon receiving the emission stop instruction, the drive circuit 14 stops the supply of drive power to the light emitting element LD2 and causes the light emitting element LD2 to stop the emission of the laser beam. In addition, the CPU 30 resets the timer B.

At Step S140, according to the above-described blood flow measuring method, the CPU 30 calculates a spectrum distribution for each frequency ω by subjecting time series data of the amount of received light of the light emitting element LD1 acquired at Step S50 to the FFT, and measures a blood flow by integrating the calculated spectrum distribution with respect to the entire frequency ω.

At Step S150, according to the above-described blood oxygen saturation measuring method, the CPU 30 stores the amount of received light of the light emitting element LD1 acquired at Step S50 and the amount of received light of the light emitting element LD2 acquired at Step S110 in a preset area of the RAM 34. Then, the CPU 30 measures the blood oxygen saturation by using the time series data of the amount of received light to calculate the equations (1) and (2) or known equations obtained by modifying these equations (1) and (2).

At Step S160, the CPU 30 determines whether or not an end instruction to end the measurement of living-body information is received. When a result of the determination at Step S160 is negative, the process returns to Step S20 and the CPU 30 continues to measure the blood flow and the blood oxygen saturation by repeating Steps S20 to S160 until the end instruction is received.

Figure 13:
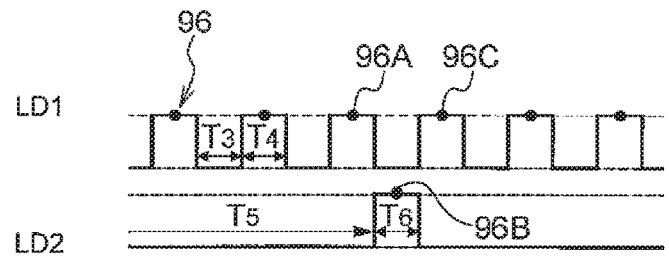
FIG. 13 is a timing chart illustrating one example of an emission timing of a light emitting element emitting IR light and a light emitting element emitting red light, and a light receiving timing of a light receiving element.

FIG. 13 is a timing chart illustrating one example of emission timings of the light emitting elements LD1 and LD2 when the living-body information measurement program of FIG. 12 is executed.

As illustrated in FIG. 13, an emission stop period having the length of time $T_3$ and an emission period having the length of time $T_4$ repeatedly appear in the light emitting element LD1. In addition, an emission stop period having the length of time $T_5$ and an emission period having the length of time $T_6$ repeatedly appear in the light emitting element LD2. However, by setting the emission stop period of the light emitting element LD2 to be longer than the emission stop period of the light emitting element LD1, a situation where the light emitting element LD2 emits light every emission period of the light emitting element LD1 may be avoided.

In this case, the measuring unit 20 measures the blood oxygen saturation by using the amount of received light of the light emitting element LD2 acquired at a light receiving point 96B among light receiving points 96 indicating acquisition timings of the amount of received light of the light emitting elements LD1 and LD2, and the amount of received light of the light emitting element LD1 acquired at one of a light receiving point 96A and the light receiving point 96B during the emission period of the light emitting element LD1 adjacent along a time axis to the emission period of the light emitting element LD2 including the light receiving point 96B.

This is because the use of the amount of received light of the light emitting element LD1 and the amount of received light of the light emitting element LD2 which are as temporarily close to each other as possible tends to increase the accuracy of measurement of oxygen saturation in the blood. Hereinafter, "the light receiving points 96 are as temporarily close to each other as possible" may be sometime simply referred to as "the light receiving points 96 are close to each other."

Although the length of the emission stop period of the light emitting element LD2 is fixed in the flow chart of the living-body information measurement program illustrated in FIG. 12, the length of the emission stop period of the light emitting element LD2 may be variable.

Figure 14:
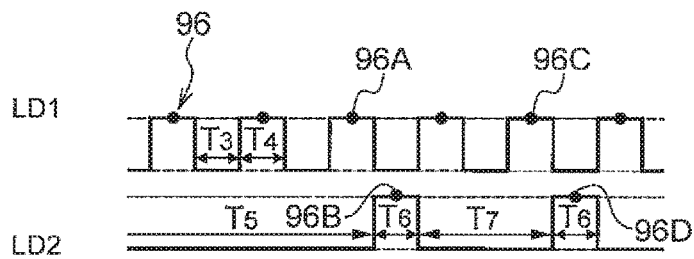
FIG. 14 is a timing chart illustrating another example of an emission timing of a light emitting element emitting IR light and a light emitting element emitting red light, and a light receiving timing of a light receiving element.

FIG. 14 is a timing chart illustrating one example of emission timings of the light emitting elements LD1 and LD2 when time $T_5$ and time $T_7$ defining the emission stop period of the light emitting element LD2 are set to different values. Even in this case, the measuring unit 20 measures the oxygen saturation in the blood by using the amount of received light of the light emitting element LD1 at the light receiving point 96A, the amount of received light of the light emitting element LD2 at the light receiving point 96B which is one example of the light receiving points 96 and is close to the light receiving point 96A, the amount of received light of the light emitting element LD1 at a light receiving point 96C, and the amount of received light of the light emitting element LD2 at a light receiving point 96D which is one example of the light receiving points 96 and is close to the light receiving point 96C.

In addition, for example, a mean value of the amount of received light at the light receiving points 96 in plural emission periods included in a specific period of the emission period of the light emitting element LD1 maybe assumed as the amount of received light in the emission period of the light emitting element LD1. In addition, a mean value of the amount of received light at the light receiving points 96 in plural emission periods included in a specific period of the emission period of the light emitting element LD2 may be assumed as the amount of received light in the emission period of the light emitting element LD2.

Figure 15:
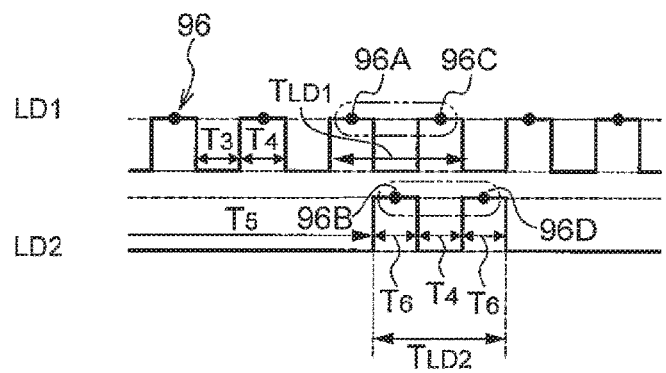
FIG. 15 is a timing chart illustrating another example of an emission timing of a light emitting element emitting IR light and a light emitting element emitting red light, and a light receiving timing of a light receiving element.

For example, as illustrated in FIG. 15, the measuring unit 20 calculates a mean value of the amount of received light at the light receiving points 96A and 96C in the respective emission periods included in a specific period $T_{LD1}$ of the emission period of the light emitting element LD1. In addition, the measuring unit 20 calculates a mean value of the amount of received light at the light receiving points 96B and 96D in the respective emission periods included in a specific period $T_{LD2}$ of the emission period of the light emitting element LD2. Then, the measuring unit 20 measures the oxygen saturation in the blood by using the mean value of the amount of received light at the light receiving points 96A and 96C and the mean value of the amount of received light at the light receiving points 96B and 96D.

Figure 16:
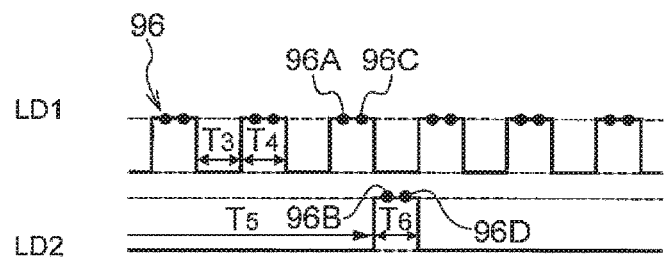
FIG. 16 is a timing chart illustrating another example of an emission timing of a light emitting element emitting IR light and a light emitting element emitting red light, and a light receiving timing of a light receiving element.

In addition, as illustrated in FIG. 16, the measuring unit 20 may set plural light receiving points 96 in the emission period of the light emitting element LD1 and the emission period of the light emitting element LD2, acquire the amount of received light at the light receiving points 96, and assume a mean value of the acquired amount of received light at the light receiving points 96 as the amount of received light in the emission periods of the light emitting elements LD1 and LD2. That is, the mean value of the amount of received light at the light receiving points 96A and 96C is assumed as the amount of received light in the emission period of the light emitting element LD1 and the mean value of the amount of received light at the light receiving points 96B and 96D is assumed as the amount of received light in the emission period of the light emitting element LD2.

Although it is illustrated in FIG. 16 that the plural light receiving points 96 are set in the emission periods of the light emitting elements LD1 and LD2 and the amount or received light at the light receiving points 96 is averaged, the method for calculating the amount of received light is not limited thereto. For example, the plural light receiving points 96 may be set in the emission period of only one of the light emitting elements LD1 and LD2.

That is, the data of the amount of received light of the light emitting elements LD1 and LD2 used for measurement are not limited to the number of data illustrated in FIG. 14. For example, as illustrated in FIG. 15, a specific period may include plural emission periods, and, as illustrated in FIG. 16, the plural light receiving points 96 may be set in the emission periods of the light emitting elements LD1 and LD2.

In this way, according to the living-body information measurement device 10 of this exemplary embodiment, it is possible to control the light emitting elements LD1 and LD2 such that the emission periods of the light emitting elements LD1 and LD2 do not overlap with each other, although the emission periods of the light emitting elements LD1 and LD2 may partially overlap with each other, and such that the number of times of emission of the light emitting element LD2 per unit time becomes less than the number of times of emission of the light emitting element LD1 per unit time.

Accordingly, it is possible to measure the bloodflow and the oxygen saturation in the blood with power less than power consumed when the emission periods of the light emitting elements LD1 and LD2 are set to be equal to each other and the light emitting elements LD1 and LD2 emit light alternately.

In addition, the living-body information measurement device 10 may be used for measurement of blood velocity, as described above. In addition, as illustrated in FIG. 7, since the amount of light received in the light receiving element 3 varies depending on the pulse of arteries, it is possible to measure a pulse rate from the variation of the amount of light received in the light receiving element 3. In addition, it is possible to measure an acceleration pulse wave by twice differentiating a waveform obtained by measuring a change in pulse rate in a chronological order. The acceleration pulse wave is used for estimation of blood vessel age, diagnosis of arteriosclerosis, or the like.

In addition, the living-body information measurement device 10 may be used for measurement of other living-body information without being limited to the above-mentioned living-body information.

In addition, although it has been illustrated in the exemplary embodiments that the processes in the control unit 12 and the measuring unit 20 are implemented with software, a process similar to the flow chart illustrated in FIG. 12 may be implemented with hardware. In this case, the processes in the control unit 12 and the measuring unit 20 may be performed more quickly than those implemented with software.

Furthermore, although it has been illustrated in the exemplary embodiments that the living-body information measurement program is installed in the ROM 32, the exemplary embodiments are not limited thereto. The living-body information measurement program according to the exemplary embodiments may be provided in the form of a computer-readable recording medium recording the program. For example, the living-body information measurement program according to the exemplary embodiments may be provided in the form of a portable recording medium recording the program, such as a compact disc (CD)-ROM, a digital versatile disc (DVD)-ROM, a universal serial bus (USB) memory or the like. Furthermore, the living-body information measurement program according to the exemplary embodiments may be provided in the form of a semiconductor memory recording the program, such as a flash memory or the like.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A living-body information measurement device comprising:
a first light emitting element configured to emit light in a first wavelength;
a second light emitting element configured to emit light in a second wavelength different than the first wavelength;
a light receiving element configured to receive the light, emitted from the first light emitting element and the second light emitting element; and
at least one hardware processor configured to implement:
controlling a first emission period of the first light emitting element and a second emission period of the second light emitting element so that a second number of times of emission of the second light emitting element per a unit of time is less than a first number of times of emission of the first light emitting element per the unit of time and so that the first light emitting element begins emitting light before the second light emitting element begins emitting light per the unit of time, which begins at a reset of at least one timer; and
measuring a plurality of living-body information based on the light received in the light receiving element.

2. The living-body information measurement device according to claim 1,
wherein the at least one hardware processor is further configured to implement:
controlling the first emission period does not overlap with the second emission period.

3. The living-body information measurement device according to claim 1,
wherein the at least one hardware processor is further configured to implement:
measuring the plurality of living-body information based on a frequency spectrum for an amount of light emitted by the first light emitting element and received in the light receiving element, an amount of light emitted by the first light emitting element and received in the light receiving element, and an amount of light emitted by the second light emitting element and received in the light receiving element.

4. The living-body information measurement device according to claim 1,
wherein the at least one hardware processor is further configured to implement:
measuring the plurality of living-body information by using a combination of an amount of received light in the first emission period of the first light emitting element and an amount of received light in the second emission period of the second light emitting element that is adjacent to the first emission period of the first light emitting element.

5. The living-body information measurement device according to claim 4,
wherein the at least one hardware processor is further configured to implement:
setting a mean value of an amount of received light in a plurality of first emission periods, including the first emission period, of the first light emitting element included in a specific period as an amount of received light in the first emission period of the first light emitting element, and
setting a mean value of an amount of received light in a plurality of emission periods, including the second emission period, of the second light emitting element, which are adjacent to the plurality of first emission periods of the first light emitting element included in the specific period, as an amount of received light in the second emission period of the second light emitting element.

6. The living-body information measurement device according to claim 4,
wherein the at least one hardware processor is further configured to implement:
acquiring an amount of received light from the light receiving element over a plurality of times in at least one of the first emission period of the first light emitting element and the second emission period of the second light emitting element, and
setting a mean value of the acquired amount of received light as the amount of received light received during a period when the amount of received light is acquired from the light receiving element during the plurality of times.

7. The living-body information measurement device according to claim 1,
wherein the at least one hardware processor configured to implement:
measuring living-body information, including at least one of a blood flow, a blood velocity and a blood volume, and an oxygen saturation in the blood, as the plurality of living-body information.

8. The living-body information measurement device according to claim 1,
wherein the at least one hardware processor is configured to:
control the first light emitting element to:
turn on at a first time,
after the first time, turn off at a second time, and
after the second time, turn on at a third time; and
control the second light emitting element to:
turn on at the third time, and
after turning on at the third time, turn off at a fourth time,
wherein there is a first length of time from the second time to the third time,
wherein there is a second length of time from the third time to the fourth time, and
wherein the second length of time is shorter than the first length of time.

9. The living-body information measurement device according to claim 1,
wherein the at least one hardware processor is further configured to:
reset a first timer and a second timer at a first time, the at least one timer being one of the first timer and the second timer;
measure a first length of time from the first time by both the first timer and the second timer;
in response to determining, at a second time after the first time, that the first length of time, indicated by the first timer, is greater than a first threshold, reset the first timer, begin measuring, by the first timer, a second length of time from the second time and control the first light emitting element to emit light;
in response to determining, at a third time after the second time, that the second length of time is greater than a second threshold, reset the first timer, turn off the first light emitting element and begin measuring a third length of time from the third time by the first timer;

in response to determining, at the third time, that the first length of time, indicated by the second timer, is greater than a third threshold, reset the second timer, begin measuring, by the second timer, a fourth length of time from the third time and control the second light emitting element to emit light; and in response to determining, at a fourth time after the third time, that the fourth length of time is greater than a fourth threshold, reset the second timer, turn off the second light emitting element and begin measuring, by the second timer, a fifth length of time from the fourth time.

10. The living-body information measurement device according to claim 1,
wherein the first light emitting element is a first laser element, and
wherein the second light emitting element is a second laser element.

11. The living-body information device according to claim 1,
wherein the at least one hardware processor is configured to implement:
controlling the first light emitting element to emit light with a constant frequency while measuring the plurality of living-body information.

12. The living-body information device according to claim 11,
wherein the constant frequency is at least twice as high as a frequency difference of a beat signal observed in the light receiving element.

13. The living-body information device according to claim 12,
wherein the at least one hardware processor is configured to implement:
controlling the second light emitting element to emit light with a frequency of about 30 Hz to about 1000 Hz.

14. A non-transitory computer readable medium storing a living-body information measurement program that causes a computer to implement:
controlling a first light emitting element to emit light in a first wavelength;
controlling a second light emitting element to emit light in the second wavelength different than the first wavelength;
controlling reception of the light, emitted from the light emitting element and the second light emitting element, by the light receiving element;
controlling a first emission period of the first light emitting element and a second emission period of the second light emitting element so that a second number of times of emission of the second light emitting element per a unit of time is less than a first number of times of emission of the first light emitting element per the unit of time and so that the first light emitting element begins emitting light before the second light emitting element begins emitting light per unit of time; and
measuring a plurality of living-body information based on the light received in light receiving element.

15. A living-body information measurement device comprising:
a first light emitting element configured to emit light in a first wavelength;
a second light emitting element configured to emit light in a second wavelength different than the first wavelength;
a light receiving element configured to receive the light, emitted from the first light emitting element and the second light emitting element; and
at least one hardware processor configured to implement:
controlling a first emission period of the first light emitting element and a second emission period of the second light emitting element so that a second number of times of emission of the second light emitting element per a unit of time is less than a first number of times of emission of the first light emitting element per the unit of time; and
measuring a plurality of living-body information based on the light received in the light receiving element,
wherein the at least one hardware processor further configured to implement:
controlling the first light emitting element to emit light with a constant frequency while measuring the plurality of living-body information.

16. The living-body information device according to claim 15,
wherein the constant frequency is at least twice as high as a frequency difference of a beat signal observed in the light receiving element.

* * * * *